United States Patent [19]

Kobayashi et al.

[11] Patent Number: 4,690,525

[45] Date of Patent: Sep. 1, 1987

[54] EYE FUNDUS CAMERA

[75] Inventors: Kazunobu Kobayashi, Yokohama; Kyoji Sekiguchi, Tokyo; Isao Matsumura, Yokosuka; Haruhisa Madate, Kawasaki, all of Japan

[73] Assignee: Canon Kabushiki Kaisha, Tokyo, Japan

[21] Appl. No.: 682,231

[22] Filed: Dec. 17, 1984

[30] Foreign Application Priority Data

Dec. 27, 1983 [JP] Japan ................................. 58-245965

[51] Int. Cl.⁴ ............................ A61B 3/14; G03B 7/00
[52] U.S. Cl. ...................................... 351/206; 354/413
[58] Field of Search .................. 351/206; 354/62, 410, 354/413

[56] References Cited

U.S. PATENT DOCUMENTS 4,429,970 2/1984 Fujiwara .............................. 351/206

Primary Examiner—Rodney B. Bovernick
Assistant Examiner—P. M. Dzierzynski
Attorney, Agent, or Firm—Fitzpatrick, Cella, Harper & Scinto

[57] ABSTRACT

An eye fundus camera is provided with an illuminating system for illuminating an eye to be examined, a photographing system for photographing the fundus of the eye to be examined, eye fundus reflected light receiving portions disposed in a plane substantially conjugate with the fundus of the eye to be examined and at a plurality of locations with a spacing greater than the dimension corresponding to the nipple diameter, and a control unit for operation-processing the outputs of the eye fundus reflected light receiving portions and automatically controlling the quantity of photo-taking light.

6 Claims, 9 Drawing Figures

EYE FUNDUS CAMERA

BACKGROUND OF THE INVENTION

1. Field of the Invention

This invention relates to an eye fundus camera in which the proper exposure for photographing is automatically controlled.

2. Description of the Prior Art

In conventional eye fundus cameras, the object is limited to the fundus of an eye and the quantity of strobo light for photographing has been manually adjusted. The individual differences in reflection were neglected and only the speed of the film used, the photographing manification, etc. were taken into account. Actually, however, the quantity of light arriving at the surface of the film varies by the differences in eye fundus pigment, by the differences between races, and by the degree of pupil scattering effected for photographing. It has been difficult to photograph the eye fundus at the proper exposure which often results in underexposed photographs.

For the reason set forth above, it is desired in incorporate an automatic exposure control into an eye fundus camera and eliminate the above-noted disadvantage. However, in the eye fundus, the reflection factor greatly differs between the nipple portion and other portions therefore, automatic exposure control cannot be adequately accomplished by the reflected light detecting method for control.

SUMMARY OF THE INVENTION

It is an object of the present invention to provide an eye fundus camera which is capable of photographing the fundus of an eye at the proper exposure with the difference in reflection factor between the nipple portion and other portions of the fundus of the eye being taken into account.

It is another object of the present invention to provide an eye fundus camera which is capable of photographing the fundus of an eye at the proper exposure irrespective of a magnification change.

It is still another object of the present invention to provide an eye fundus camera in which exposure control is provided during normal photography, while exposure control is not provided during fluorescence photography.

DESCRIPTION OF THE PREFERRED EMBODIMENTS

Figure 1:
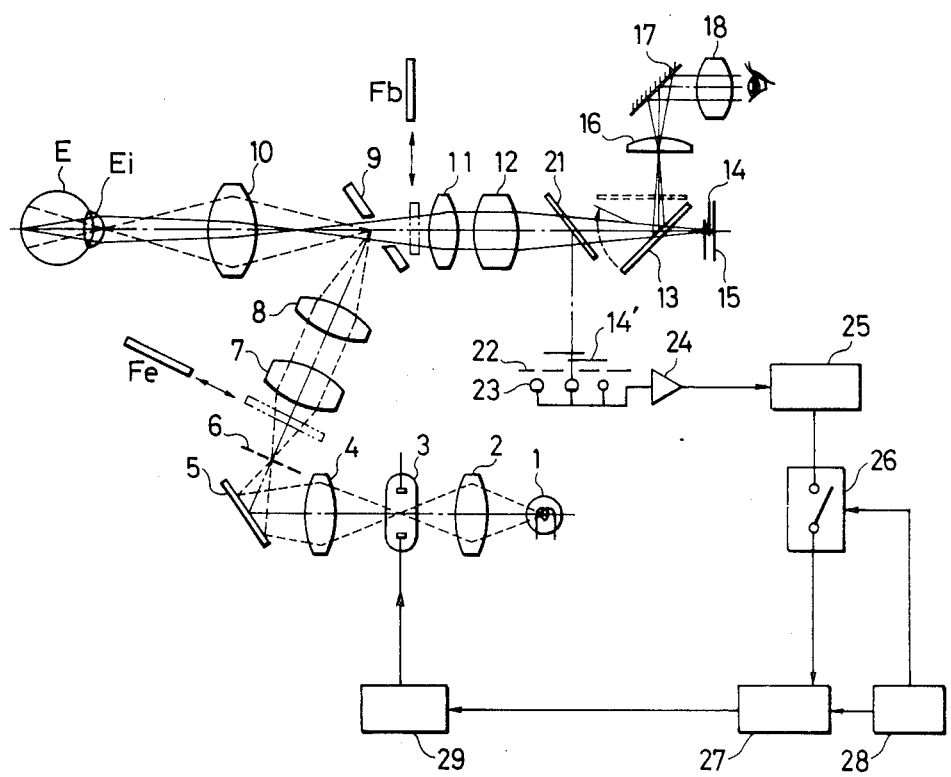
FIG. 1 shows a first embodiment of the eye fundus camera of the present invention.

Referring to FIG. 1, a fundus camera is illustrated having a filament lamp 1 which is a light source for observation, a condenser lens 2, a strobo tube 3 which is a light source for photographing, a condenser lens 4 for imaging the images of the filament lamp 1 and strobo tube 3 at the position of a ring slit 6 through the intermediary of a mirror 5, and relay lenses 7 and 8 for imaging the image at ring slit 6 at the position of an apertured mirror 9. An illuminating light travels toward an eye E from apertured mirror 9 and is caused to enter a pupil Ei of an eye E to be examined by objective lens 10 and illuminates the fundus of the eye.

The reflected light from the eye fundus illuminated in this manner now travels from eye E toward apertured mirror 9 along the above-described optical path. That is, such reflected light passes through the pupil of the eye and is once imaged by objective lens 10, and further passes through the central aperture of apertured mirror 9 and is imaged on a film 15 by a focus lens 11 and a photo-taking lens 12. A shutter 14 is provided immediately in front of film 15, and a movable mirror 13 is in its solid-line position for the purpose of alignment or focusing before photographing, and an aerial image formed at a position conjugate with the film surface may be observed by an examiner through a field lens 16, a mirror 17 and an eyepiece 18. When photographing, movable mirror 13 is pivotally moved to its dot-and-dash line position, shutter 14 is opened, strobo tube 3 is caused to emit light and film 15 is exposed to light.

Figure 2:
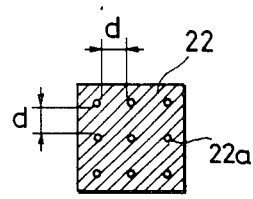
FIG. 2 is a plan view of the light-intercepting plate of FIG. 1.

Further, a shutter 14' adapted to be opened and closed in synchronism with shutter 14, is illustrated along with a beam splitter 21, and a light-intercepting plate 22 having a plurality of small openings 22a as shown in the plan view of FIG. 2, and placed at a position substantially conjugate with the film surface.

The spacing d between adjacent small openings 22a is selected having a value greater than the dimension corresponding to the nipple diameter of the eye fundus image formed on this portion. The dimension corresponding to the nipple diameter is the value of the nipple diameter multiplied by the imaging magnification. The nipple diameter is about 1.6 mm. Reference numeral 23 designates photoelectric elements. In the present embodiment, a plurality of independent elements corresponding to the plurality of (nine) small openings are provided so that the outputs thereof are added together. The output signals thereof are applied to a controller 27 through an amplifier 24, an integrator 25 for time-intergrating the output signals, and an inhibiting circuit 26. An input unit 28 receives inputs of film speed and a photographing mode such as color photography or fluorescence photography.

Inhibiting circuit 26 cuts off the circuit to controller 27 when the fluorescence photography mode is selected by input unit 28. A light source unit 29 is used as the photographing light source.

With the above-described construction, for normal photography such as color photography or monochromatic photography, at least a part of the eye fundus reflected light of the light from the photographing light source is detected. A closed loop auto strobo function for discontinuing the light emission of the strobo tube can be formed when the exposure of the film becomes proper.

The reason why a plurality of small openings 22a are provided in light-intercepting plate 22 and the spacing therebetween is determined as previously described is that the deflection factor of the eye fundus is several times higher in the nipple than in the other portion.

However the proper exposure is evaluated in the portions other than the nipple and therefore, of a plurality of detecting regions, only one region overlapes the nipple region to reduce its influence. It is desirable that the size of each small opening 22a be of such a degree that it is not buried in the blood vessel portion of the eye fundus (having a width of about 0.15 mm), that is, the diameter of each small opening 22a be 0.15 mm or more on the eye fundus. This is because the reflection factor generally differs between the blood vessel portion and the circumferential portion thereof.

An optical system, may be disposed between beam splitter 21 and light-intercepting plate 22 to vary the real dimension of spacing d of FIG. 2 and the size of photoelectric elements 23. Photoelectric elements 23 may also be a single element and, if it is imaged on a reduced scale by the optical system, a small single element may be used.

An exciter filter Fe is disposed in the illuminating optical path to excite the fluorescent agent which occurs for fluorescence photography and a barrier filter Fb is provided for causing only the excited fluorescence to arrive at the film side.

In the case of fluorescence photography, a photograph of an exposure amount corresponding to the amount of fluorescent agent which has arrived at the eye fundus is desired and therefore, the auto strobo function has been released by inhibiting circuit 26 as previously described. However, in response to the insertion of the aforementioned filter Fe or Fb into the optical path, such release may be effected, for example, by the closing signal of a switch (not shown) instead of the input signal from input unit 28 to inhibiting circuit 26.

In the present embodiment, photoelectric elements 23 may be small elements, which is advantageous with respect to the elimination of noise and providing economy.

The influence of the nipple portion is reduced by increasing the number of light-receiving portions.

In the present embodiment, shutter 14' disposed immediately in front of photoelectric elements 23 is opened and closed in synchronism with shutter 14 disposed immediately in front of film 15 and therefore, the exposure control system is designed to operate only during photography. However, instead of using the shutter 14', the exposure control system may be designed to operate electrically in synchronism with a photographing signal.

Figure 3:
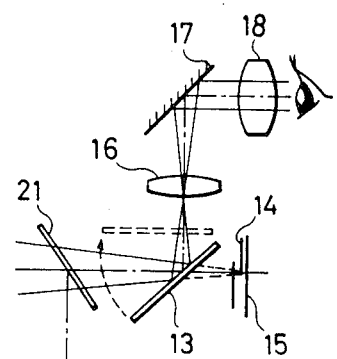
FIG. 3 shows another embodiment of the eye fundus camera having the same optical system as that shown in FIG. 1.
Figure 4:
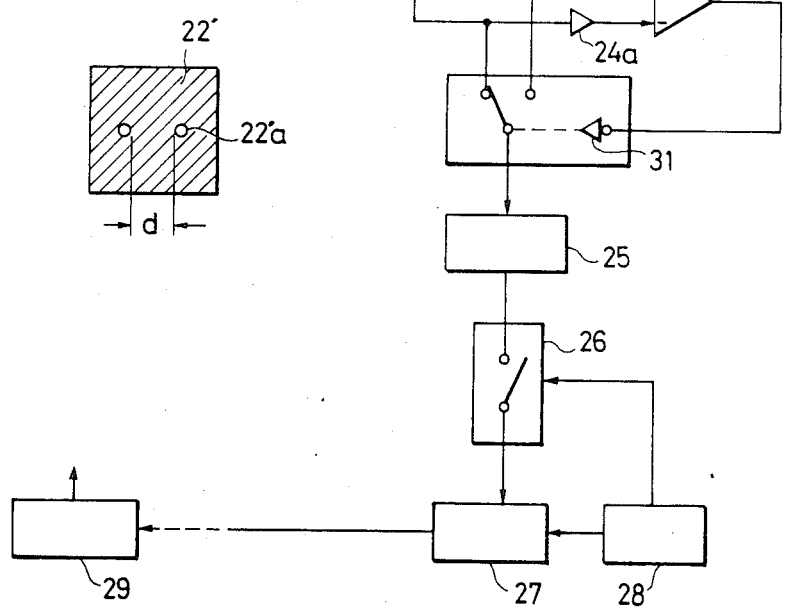
FIG. 4 is a plan view of another light-intercepting plate in FIG. 3.

FIG. 3 shows another embodiment of the present invention. A light-intercepting plate 22', as shown in the plan view of FIG. 4, has two small openings 22'a spaced apart from each other by a spacing d greater than the dimension corresponding to the nipple diameter of the eye fundus image formed on this portion. Separate photoelectric elements 23a and 23b are provided correspondingly to the two small openings, and the output signals thereof pass through amplifiers 24a and 24b, respectively, and arrive at an integrator 25 through a comparator 30 and an analog switch 31. The behavior of these output signals thereafter is similar to what has been described in connection with FIG. 1.

Comparator 30 is adapted to detect which of the signals from photoelectric elements 23a and 23b is lower and operate analog switch 31 by that output signal and cause the lower output signal of photoelectric element 23a or 23b to arrive at integrator 25.

Therefore, even if the nipple portion is imaged in one of the two small openings 22'a, the exposure amount is not controlled by the output signal from this portion and thus, the exposure amount is controlled by the reflected light from the region of the eye fundus other than the nipple. In the present embodiment, two small openings have been shown, but three or more such openings may be provided, and the exposure control based on the region other than the nipple portion is accomplished by taking off a maximum output signal from the exposure controlling signal. That is, if n small openings are provided, use may be made of (n−1) outputs except the maximum output and the exposure may be controlled, for example, by taking the average value thereof.

Figure 5:
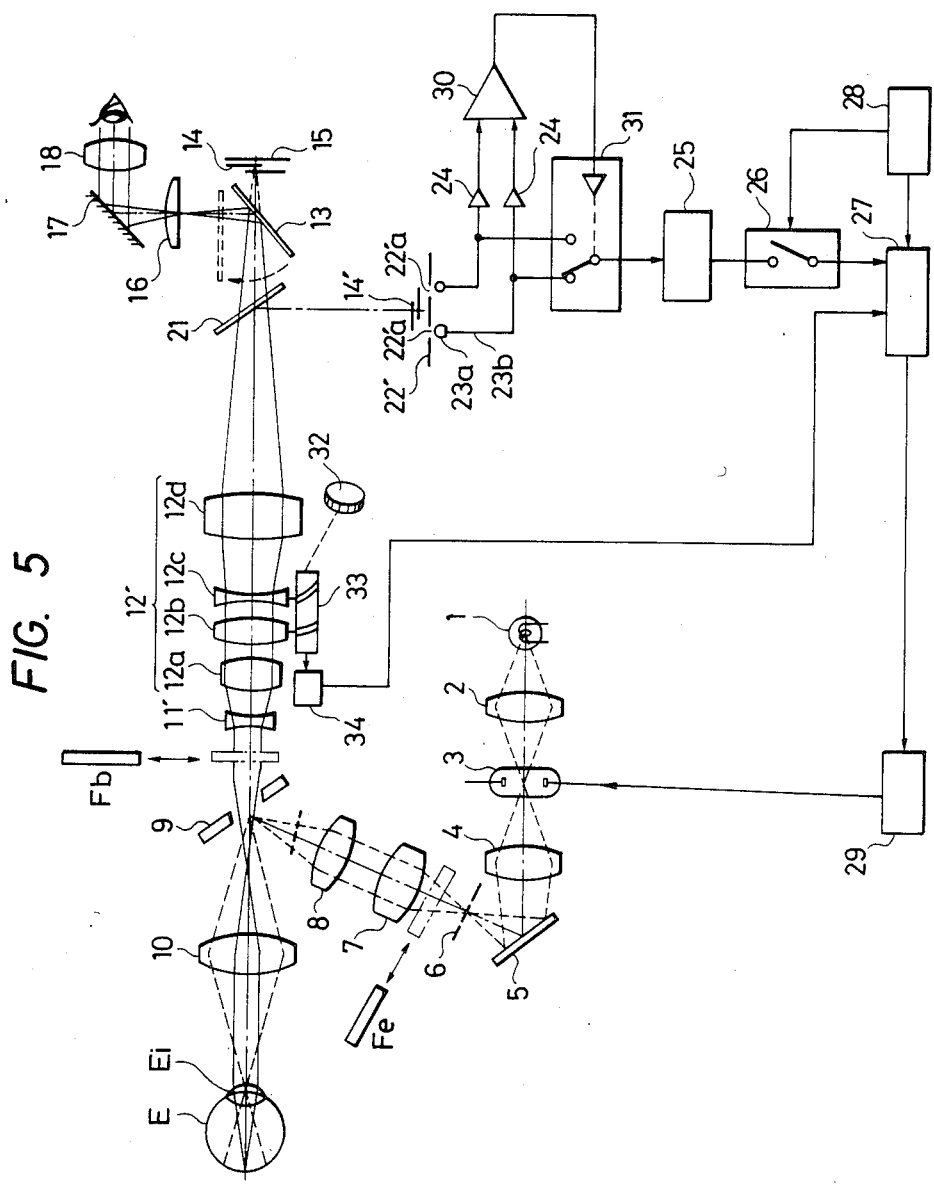
FIG. 5 shows still another embodiment of the eye fundus camera having a magnification changing optical system in the photographing system thereof.

FIG. 5 shows an embodiment of an eye fundus camera having a magnification changing optical system in the photographing system thereof.

In FIG. 5, the eye fundus camera has a focus lens 11', and a zoom lens 12' comprising fixed lenses 12a, 12d, a variator 12b and an extender 12c.

A cam 33 is rotated by rotation of a magnification changing knob 32, and variator 12b and extender 12c are moved in a predetermined relation, whereby the eye fundus image magnification on the imaging plane is varied.

In the present embodiment, it is a condition that even if the eye fundus image is projected at its greatest magnification, the spacing between the aforementioned two small openings 22'a is greater than the dimension corresponding to the then nipple diameter. This also holds true in a case where three or more small openings are provided, and in such case, the spacing between any two small openings is set so as to be greater than the dimension corresponding to the nipple diameter. Thereby the aforedescribed exposure control is accomplished in spite of a magnification change. In the present embodiment, design is made such that the output signal from magnification change amount detector 34 such as a potentiometer operatively associated with cam 33 is also caused to arrive at controller 27 so that a proper exposure is provided even if the photographing magnification is varied.

The above-described embodiments are such that the photo-taking light is detected to control its value, while embodiments shown in FIGS. 6 to 9 are such that the observation light is detected to control the quantity of photo-taking light.

Figure 6:
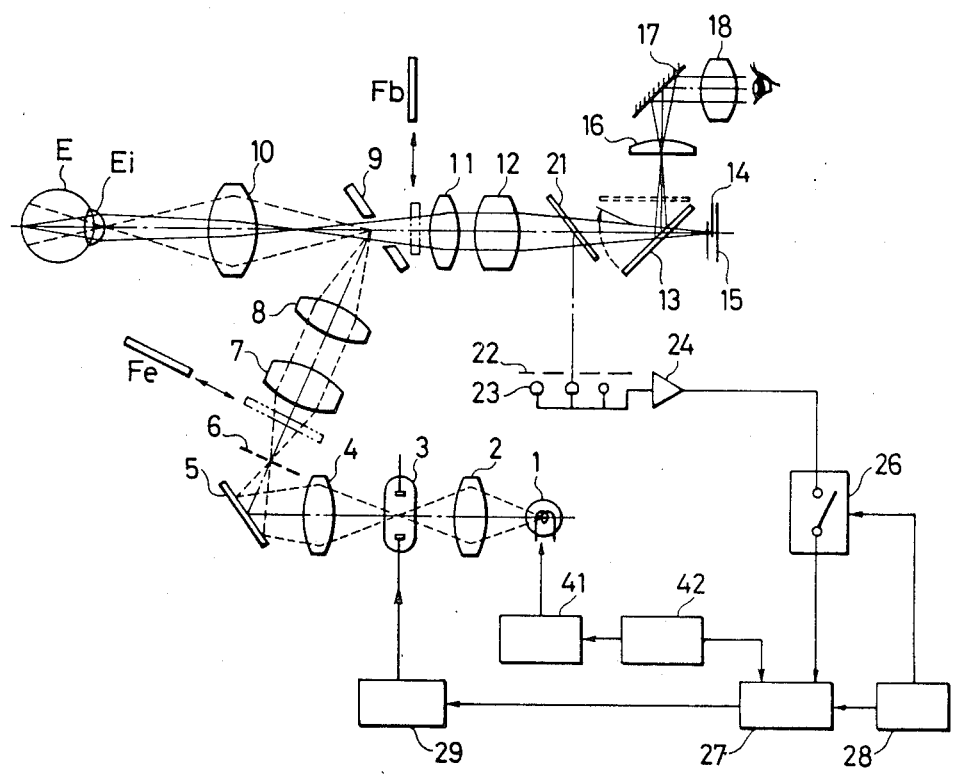
FIGS. 6 to 9 show further embodiments of the present invention.

In FIG. 6, shutter 14' and integrator 25 shown in FIG. 1 are eliminated and an observation light power source unit 41 and an observation light controller 42 are added. Observation light controller 42 controls light source 1 for observation and also transmits the degree of control of the quantity of light to controller 27.

In this embodiment, the reflected light from the fundus of the eye to be examined by the observation light is detected, and in accordance with the output thereof, the light emission of strobo tube 3 is controlled.

Figure 7:
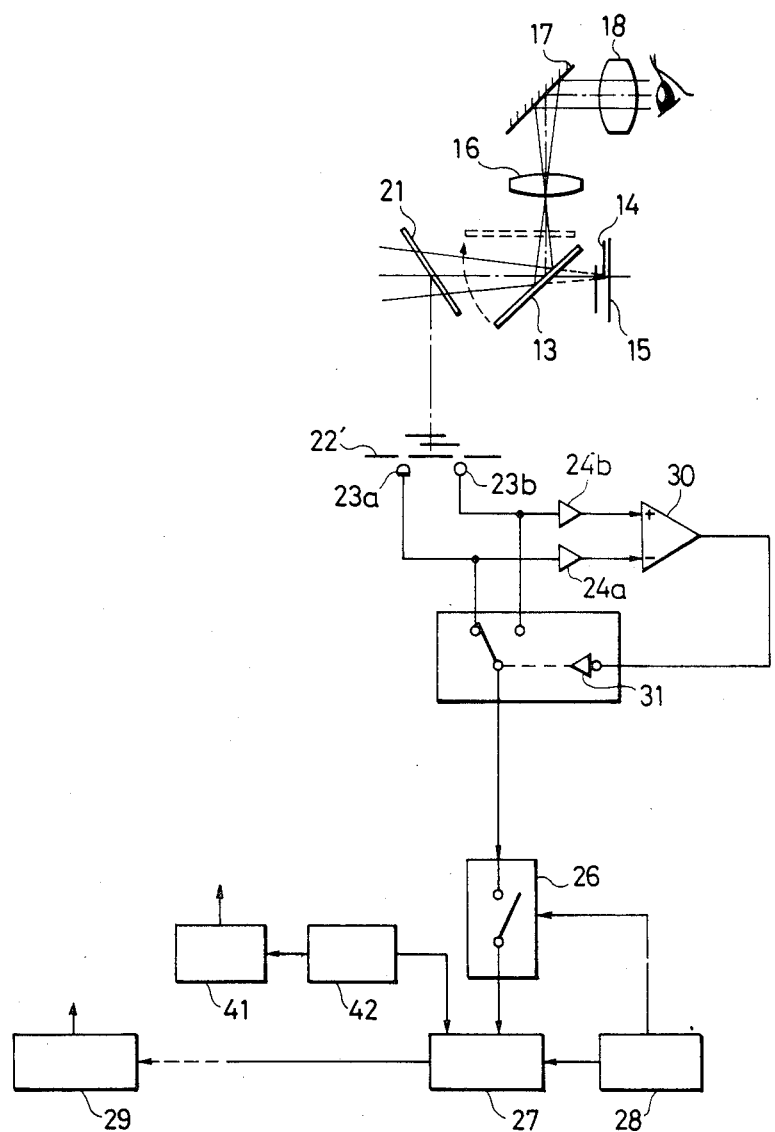
Figure 8:
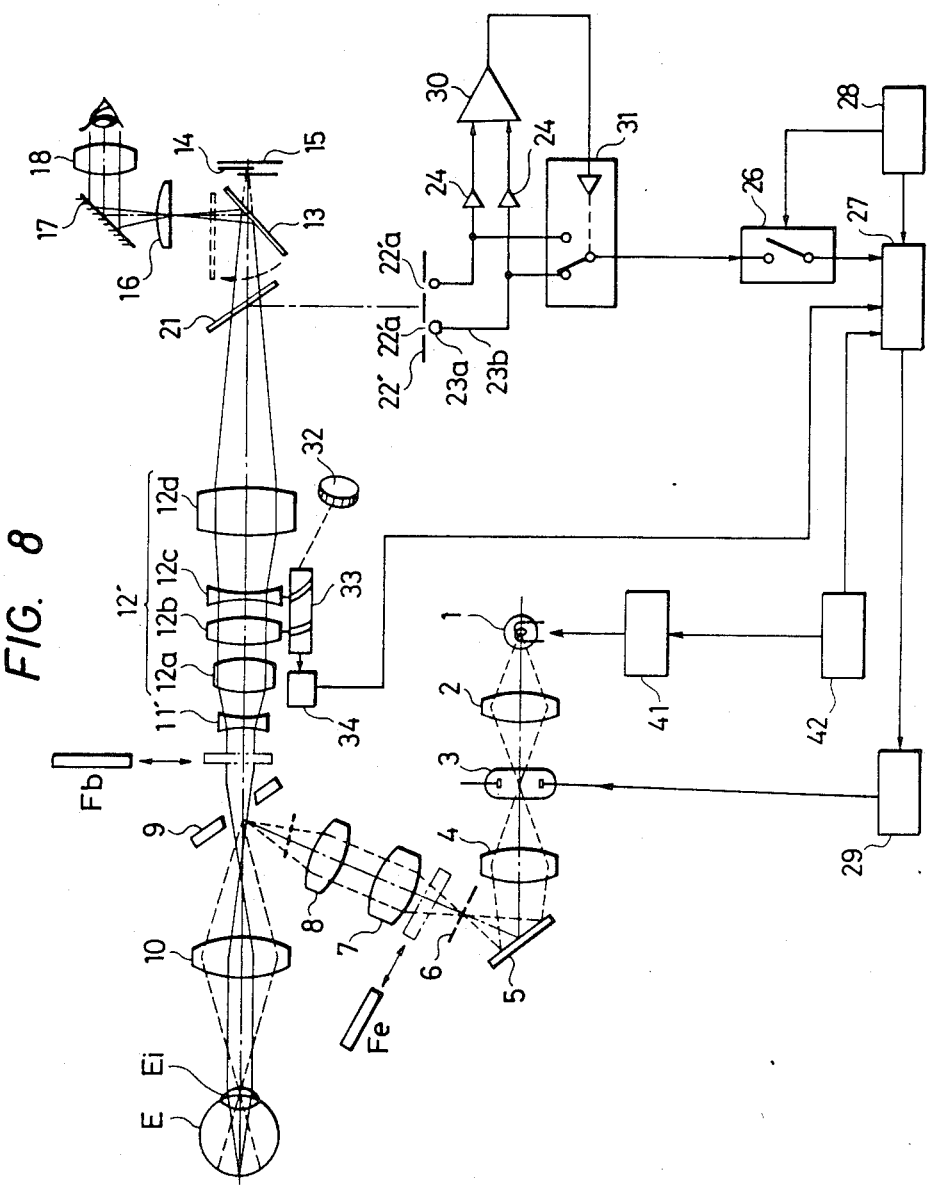
Figure 9:
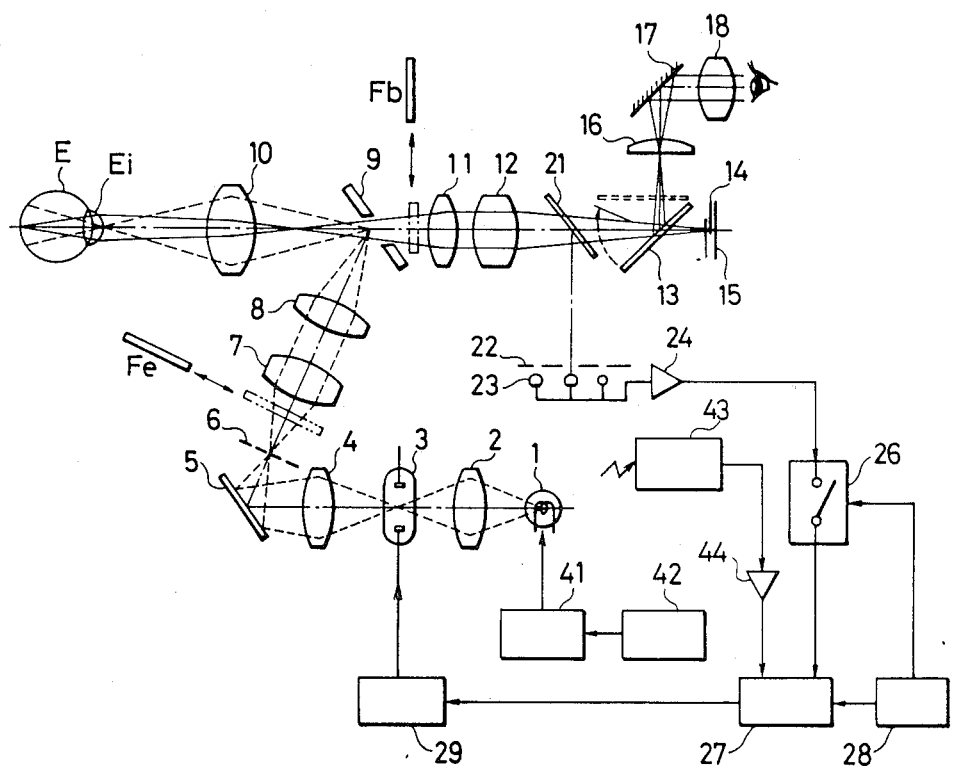

FIGS. 7 and 8 illustrate embodiments in which the observation light is likewise detected to control the quantity of photo-taking light and which correspond to the embodiments of FIGS. 3 and 5. FIG. 9 shows a modification of the FIG. 6 embodiment. In this modification, the signal of observation light controller 42 is not directly transmitted to controller 27, but a part of the quantity of light emitted from light source 1 for observation is detected by a photodetector 43 and the output thereof is transmitted to controller 27 through an amplifier 44. Thereby, the reduction in quantity of light resulting from the aging of light source 1 for observation can also be corrected. Photodetector 43 may be provided at a position in the illuminating optical path, which is not conjugate with the eye fundus, directly or through a suitable beam splitter. This is also applicable to the embodiments corresponding to FIGS. 7 and 8.

We claim:

1. An eye fundus camera having:
    an illuminating system for illuminating an eye to be examined;
    a photographing system for photographing the fundus of the eye to be examined;
    light receiving portions comprising multiple spots for receiving the reflected light from the eye fundus illuminated by said illuminating system, said light receiving portions being disposed in a plane substantially optically conjugate with the fundus of the eye to be examined, the spacing between each two adjacent spots being greater than a length corresponding to a diameter of the optic disk of the eye fundus; and
    a control unit for processing the outputs of said light receiving portions to restrict influence of the optic disk, and automatically controlling the quantity of photographing light.

2. An eye fundus camera according to claim 1, wherein said control unit time-integrates the outputs of said light receiving portions and automatically controls the quantity of photographing light.

3. An eye fundus camera according to claim 1, wherein said control unit introduces thereinto a detection signal other than a detection signal which represents the maximum reflected light received at any one spot of said light receiving portions.

4. An eye fundus camera having:
    an illuminating system for illuminating an eye to be examined;
    a variable magnification photographing system for photographing the fundus of the eye to be examined at a variable magnification;
    light receiving portions comprising multiple spots for receiving the reflected light from the eye fundus illuminated by said illuminating system, said light receiving portions being disposed in a plane substantially optically conjugate with the fundus of the eye to be examined, the spacing between each two adjacent spots being greater than a length corresponding to a diameter of the optic disk of the eye fundus; and
    a control unit for processing the outputs of said light receiving portions to restrict influence of the optic disk, and automatically controlling the quantity of photographing light.

5. An eye fundus camera capable of fluorescence photography and normal photography, said camera having:
    an illuminating system for photographing the fundus of the eye to be examined;
    light receiving portions comprising multiple spots for receiving the reflected light from the eye fundus illuminated by said illuminating system, said light receiving portions being disposed in a plane substantially optically conjugate with the fundus of the eye to be examined, the spacing between each two adjacent spots being greater than a length corresponding to a diameter of the optic disk of the eye fundus; and
    a control unit for processing the outputs of said light receiving portions to restrict influence of the optic disk, and automatically controlling the quantity of photographing light.

6. An eye fundus camera having:
    an illuminating system for illuminating an eye to be examined; and
    a photographing system for photographing the fundus of the eye to be examined;
    light receiving portions including multiple spots for receiving the reflected light from the eye fundus illuminated by said illuminating system, said light receiving portions being disposed in a plane substantially optically conjugate with the fundus of the eye to be examined, the spacing between each two adjacent spots being so determined that no more than one of said spots is influenced by the reflected light from the optic disk of the eye fundus.

* * * * *